(12) United States Patent
Bergmann

(10) Patent No.: US 7,572,590 B2
(45) Date of Patent: Aug. 11, 2009

(54) METHOD FOR THE DIAGNOSIS OF SEPSIS WITH DETERMINATION OF CA 19-9

(75) Inventor: Andreas Bergmann, Berlin (DE)

(73) Assignee: B.R.A.H.M.S. Aktiengesellschaft, Henningsdorf (DE)

( * ) Notice: Subject to any disclaimer, the term of this patent is extended or adjusted under 35 U.S.C. 154(b) by 385 days.

(21) Appl. No.: 10/496,250

(22) PCT Filed: Nov. 27, 2002

(86) PCT No.: PCT/EP02/13392

§ 371 (c)(1),
(2), (4) Date: Nov. 5, 2004

(87) PCT Pub. No.: WO03/048777

PCT Pub. Date: Jun. 12, 2003

(65) Prior Publication Data

US 2005/0059104 A1 Mar. 17, 2005

(30) Foreign Application Priority Data

Dec. 4, 2001 (EP) ................................. 01128850

(51) Int. Cl.
*G01N 33/53* (2006.01)
*G01N 33/48* (2006.01)
(52) U.S. Cl. ......................................... 435/7.1; 702/19
(58) Field of Classification Search .................. 435/7.1; 702/19
See application file for complete search history.

(56) References Cited

U.S. PATENT DOCUMENTS

| 5,639,617 A | 6/1997 | Bohuon ....................... 435/7.1 |
| 5,660,994 A | 8/1997 | Bruder-Heid et al. ...... 435/7.23 |

FOREIGN PATENT DOCUMENTS

| DE | 198 47 690 A1 | 4/2000 |
| DE | 101 19 804 A1 | 10/2002 |
| DE | 101 30 985 A1 | 1/2003 |
| DE | 101 31 922 A1 | 1/2003 |
| EP | 1 318 404 B1 | 7/2004 |
| WO | WO 00/22439 | 4/2000 |
| WO | WO 02/085937 A2 | 10/2002 |
| WO | WO 03/002600 A1 | 1/2003 |
| WO | WO 03/005035 A1 | 1/2003 |

OTHER PUBLICATIONS

Aird, "The Hematologic System as a Marker of Organ Dysfunction in Sepsis," *Mayo Clin, Proc.*, 78:869-881, 2003.
Assicot, et al., "High Serum Procalcitonin Concentrations in Patients with Sepsis and Infection," *Lancet*, 341(8844):515-518, 1993.
Beishuizen et al., "Endogenous Mediators in Sepsis and Septic Shock," *Advances Clin. Chem.*, 33:55-131, 1999.
Carrigan et al., "Toward Resolving the Challenges of Sepsis Diagnosis," *Clin. Chem.*, 50(8):1301-1314, 2004.
Gabay and Kushner, "Acute-Phase Proteins and Other Systemic Responses to Inflammation," *New Engl. J. Med.*, 340(6):448-454, 1999.
Hotchkiss and Karl, "The Pathophysiology and Treatment of Sepsis," *N. Engl. J. Med.*, 348(2):138-150, 2003.
Karzai, et al., "Procalcitonin—A New Indicator of the Systemic Response to Severe Infections," *Infection*, 25:3-8, 1997.
Ker et al., "Assessment of Serum and Bile Levels of CA19-9 and CA125 in Cholangitis and Bile Duct Carcinoma," *J. Gastro. Hepta.*, 6:505-508, 1991.
Lab Tests Online, CA 19-9, Internet document, last modified Jun. 26, 2002.
Lamerz, "CA 19-9, GICA (Gastrointestinal Cancer Antigen)" Labor and Diagnose, Section 34.3, $5^{th}$ Edition, Ed. Lother Thomas, TH-Books Verlagsgesellschaft, 1998, p. 966-969.
Marshall et al., "Measures, Markers, and Mediators: Toward a Staging System for Clinical Sepsis. A Report of the Fifth Toronto Sepsis Roundtable, Toronto, Ontario, Canada, Oct. 25-26, 2000," *Crit. Care Med.*, 31(5):1560-1567, 2003 (Abstract only).
Oberholzer et al., "Sepsis Syndromes: Understanding the Role of Innate and Acquired Immunity," *Shock*, 16(2):83-96, 2001 (Abstract only).
Oczenski et al., "Procalcitonin: A New Parameter for the Diagnosis of Bacterial Infection in the Peri-Operative Period," *Eur. J. Anaesthesiol.*, 15:202-209, 1998.
Pfister et al., "Elevated Carbohydrate Antigen 19-9 (CA 19-9) in Patients with Echinococcus Infection," *Clin. Chem. Lab Med.*, 39(6):527-530, 2001.
Redl et al., "Procalcitonin Release Patterns in a Baboon Model of Trauma and Sepsis: Relationship to Cytokines and Neopterin," *Crit. Care Med.*, 28(11):3659-3663, 2000.
Redl and Schlag, "Non-Human Primate Models of Sepsis," *Sepsis*, 2:243-253, 1998.
Reinhart et al., "Sepsis Und Spetischer Schcok," *Intensivmedizin*, 756-760, 2001.
International Search Report for EPO Application No. 01128850.3, mailed Jun. 4, 2002.
International Search Report for PCT Application No. PCT/EP 02/13392, mailed Mar. 11, 2003.

*Primary Examiner*—Jerry Lin
(74) *Attorney, Agent, or Firm*—Heslin Rothernberg Farley & Mesiti P.C.

(57) ABSTRACT

Method for early differential diagnosis and detection, prognosis and assessment of the severity and therapy-accompanying assessment of the course of sepsis and sepsis-like systemic infections, in which, preferably with determination of at least one further parameter suitable for sepsis diagnosis, the amount of CA 19-9 in a biological fluid of a patient who is suffering from sepsis or is suspected of having sepsis is determined and conclusions are drawn from the determined amount of CA 19-9 with regard to the presence, the expected course, the severity and/or the success of initiated measures for the treatment of the sepsis.

9 Claims, 2 Drawing Sheets

METHOD FOR THE DIAGNOSIS OF SEPSIS WITH DETERMINATION OF CA 19-9

Figure 1:
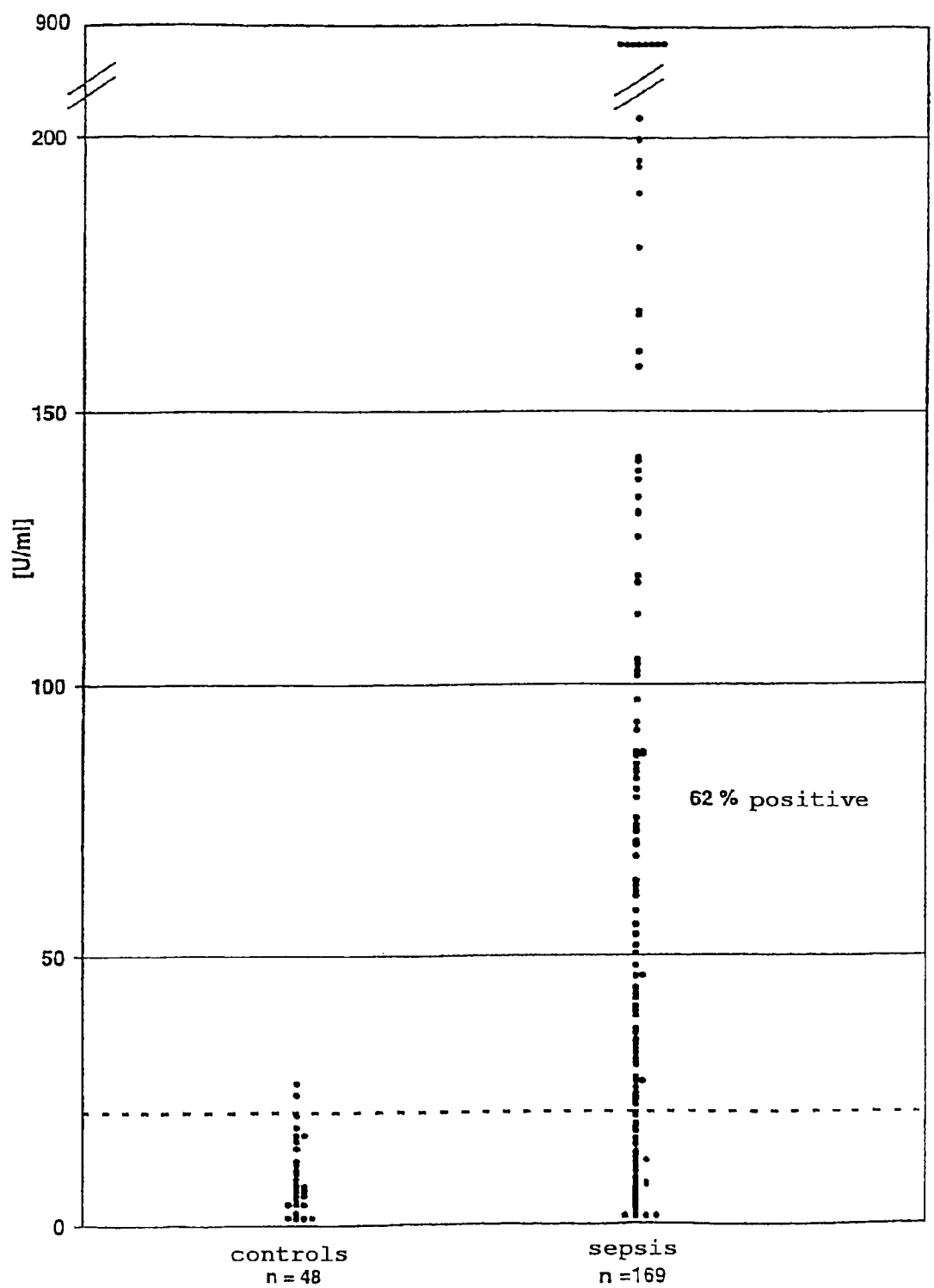

The present application is a nationalization of PCT Application Serial No. PCT/EP02/13392, filed Nov. 27, 2002, which claims priority to European application No. 01128850.3, filed Dec. 4, 2001.

The invention relates to a novel method for sepsis diagnosis, in which, or in the course of which, the parameter CA 19-9 known per se as a typical tumour marker in medical diagnosis is determined.

The invention is based on the detection for the first time of greatly increased concentrations of CA 19-9 in sera of patients who have been diagnosed as having a sepsis on the basis of clinical findings with simultaneously increased serum concentrations of the known sepsis marker procalcitonin.

The present invention has its origin in intensive research work by the Applicant in relation to further improvements of the diagnosis and therapy of inflammations of infectious aetiology and sepsis.

Inflammations are defined very generally as certain physiological reactions of an organism to different types of external effects, such as, for example, injuries, burns, allergens, infections by microorganisms, such as bacteria and fungi and viruses, to foreign tissues which trigger rejection reactions, or to certain inflammatory endogenous conditions of the body, for example in autoimmune diseases and cancer. Inflammation may occur as harmless, localized reactions of the body but also typical features of numerous serious chronic and acute diseases of individual tissues, organs, organ parts and tissue parts.

In sepsis or septic shock, inflammation-specific reaction cascades spread in an uncontrolled manner over the whole body and may become life-threatening in the context of an excessive immune response. Regarding the current knowledge about the occurrence and the possible role of individual groups of endogenous sepsis-specific substances, reference is made, for example, to A. Beishuizen et al., "Endogenous Mediators in Sepsis and Septic Shock", Advances in Clinical Chemistry, Vol. 33, 1999, 55-131; and C. Gabay et al., "Acute Phase Proteins and Other Systemic Responses to Inflammation", The New England Journal of Medicine, Vol. 340, No. 6, 1999, 448-454. Since the understanding of sepsis and related systemic inflammatory diseases, and hence also the recognized definitions, have changed in recent years, reference is also made to K. Reinhart et al., "Sepsis and septischer Schock" [Sepsis and septic shock], in: Intensivmedizin, Georg Thieme Verlag, Stuttgart, New York, 2001, 756-760, where a modern definition of sepsis is given. In the context of the present invention, the term sepsis used is based on the definitions given in the stated references.

Whereas at least in Europe the systemic bacterial infection detectable by a positive blood culture long characterized the term sepsis, sepsis is now primarily understood as being systemic inflammation which is caused by infection. Said transformation in the understanding of sepsis has resulted in changes in the diagnostic approaches. Thus, the direct detection of bacterial pathogens was replaced or supplemented by complex monitoring of physiological parameters and, more recently, in particular by the detection of certain endogenous substances involved in the sepsis process or in the inflammatory process, i.e. specific "biomarkers".

Of the large number of mediators and acute phase proteins which are known to be, or presumed to be, involved in an inflammatory process, the ones which are suitable for purposes of clinical sepsis diagnosis are in particular those which occur with high sensitivity and specificity in sepsis or certain phases of a sepsis or whose concentrations change in a dramatic and diagnostically significant manner and which moreover have the stabilities required for routine determinations and reach high concentration values. For diagnostic purposes, the reliable correlation of pathological process with the respective biomarker is of primary importance, without there being any need to know exactly its role in the complex cascade of the endogenous substances involved in the sepsis process.

A known endogenous substance particularly suitable as a sepsis biomarker is procalcitonin. Procalcitonin is a prohormone whose serum concentrations reach very high values under the conditions of a systemic inflammation of infectious aetiology, whereas it is virtually undetectable in healthy persons. High values of procalcitonin are also reached in a relatively early stage of a sepsis so that the determination of procalcitonin is also suitable for early diagnosis of a sepsis and for early distinguishing of a sepsis caused by infection from severe inflammations which have other causes. The procalcitonin determination is furthermore particularly valuable for therapy-accompanying observation of the course of a sepsis. The determination of procalcitonin as a sepsis marker is the subject of the publication by M. Assicot et al., "High serum procalcitonin concentrations in patients with sepsis and infection", The Lancet, Vol. 341, No. 8844, 1993, 515-518; and the patents DE 42 27 454 C2 and EP0 656 121 B1 and U.S. Pat. No. 5,639,617. Reference is hereby made expressly to said patents and to early literature references mentioned in said publication for supplementing the present description. In recent years, the number of publications on the subject of procalcitonin has greatly increased. Reference is therefore also made to W. Karzai et al., "Procalcitonin—A New Indicator of the Systemic Response to Severe Infection", Infection, Vol. 35, 1997, 329-334; and M. Oczenski et al., "Procalcitonin: a new parameter for the diagnosis of bacterial infection in the peri-operative period", European Journal of Anaesthesiology 1998, 15, 202-209; and furthermore H. Redl et al., "Procalcitonin release patterns in a baboon model of trauma and sepsis: Relationship to cytokines and neopterin", Crit Care Med 2000, Vol. 28, No. 11, 3659-3663; and H. Redl et al., "Non-Human Primate Models of Sepsis", in: Sepsis 1998; 2:243-253; and the further literature references cited therein, as typical of recent published reviews.

The availability of the sepsis marker procalcitonin has given considerable impetus to sepsis research, and intensive efforts are now being made by the Applicant to find further biomarkers which can supplement the procalcitonin determination and/or are capable of providing additional information for purposes of fine diagnosis or differential diagnosis. Thus, a search is being made in particular for further biomarkers for sepsis diagnosis, whose serum or plasma levels are regularly increased but whose determination does not simply duplicate the results of the procalcitonin determination but provides additional information, in particular on the stage of the sepsis process, i.e. information which can rather be assigned to the progress of the sepsis, and/or on the initial or principal organ of a septic process, i.e. localizing information. The aim is in the end the selection of a set of sepsis parameters which are simultaneously determined in the case of sepsis patients or potential sepsis patients, for example using the so-called chip technology or immunochromatographic methods ("point of care" or POC determinations), and in their totality provide an information pattern which clearly surpasses the information value of the determination of only one individual parameter.

The search for potential novel sepsis biomarkers is, however, complicated by the fact that frequently very little or nothing is known about the exact function or about the exact reasons for the occurrence of certain endogenous substances which are involved in the inflammatory or septic process.

Since the endogenous substances increased during sepsis are part of the complex reaction cascade of the body, not only are such substances also of diagnostic interest but attempts are currently also being made, with considerable effort, to intervene therapeutically in the sepsis process by influencing the formation and/or the concentration of individual substances of this type, in order to stop as early as possible the systemic spread of the inflammation, which spread is observed, for example, during sepsis. In this context, endogenous substances which have been shown to be involved in the sepsis process are also to be regarded as potential therapeutic targets.

The results of the experimental testing of a fruitful purely hypothetical approach to the determination of further potential sepsis markers are to be found in DE 198 47 690 A1 and WO 00/22439. There, it is shown that, in the case of sepsis, not only is the concentration of the prohormone calcitonin significantly increased but also significantly increased concentrations can be observed for other substances which may be included among the peptide prohormones. In particular, the peptide prohormones pro-enkephalin, pro-gastrin-releasing peptide (proGRP), pro-endothelin-1, pro-brain-natriuretic-peptide (pro-BNP), pro-atrial-natriuretic-peptide (pro-ANP), pro-leptin, pro-neuropeptide-Y, pro-somatostatin, pro-neuropeptide-YY, pro-interleukin-6 or pro-interleukin-10 may be mentioned in this context. While the phenomenon described is well documented, the causes of the increase in the concentrations of prohormones during sepsis are still substantially unexplained.

In the present Application, a result of another hypothetical approach in the search for further biomolecules suitable for sepsis diagnosis is now reported. It is based on the results of measurements of the physiological concentrations of biomarkers, which have been regarded to date as typical tumour markers and have therefore been clinically determined substantially for purposes of tumour diagnosis, in biological samples, in particular serum samples, of sepsis patients for whom no clinical findings at all indicate the presence of tumours.

Surprisingly, it has been found that some biomolecules regarded to date as typical tumour markers are also significantly increased in sepsis. This indicates that these are not formed in a tumour-specific manner but rather indicate a critical physiological process which also affects tissues or organs which release these tumour markers. Although all the concentrations of the biomolecules in question are increased during sepsis with high sensitivity, as shown in this Application and simultaneously filed further Applications, there is at the same time no correlation of the measured values with the likewise significantly increased procalcitonin concentrations, i.e. both parameters are found to be increased in individual patients but in some cases to very different extents.

The present invention is based on the evidence, obtained for the first time, that significantly increased physiological concentrations of CA 19-9 are found in the case of bacterial sepsis, which makes these parameters, particularly in combination with the determination of further sepsis parameters, suitable for differential sepsis diagnosis.

The method according to the invention and certain preferred embodiments thereof are defined in more detail in Claims 1 to 6.

It was not known to date that the measurable concentrations of CA 19-9, in particular serum concentrations, are significantly increased in the case of sepsis and that a determination of the concentration of CA 19-9 may therefore also be important for sepsis diagnosis.

On the basis of the present invention, it is possible to use the determination of CA 19-9 also in the course of a diagnostic sepsis test method. Of particular interest is the suitability of CA 19-9 as a prognosis marker and marker for monitoring the course of sepsis, in particular as part of a combination measurement with other markers.

In addition to a combination with a procalcitonin measurement, a combination of the measurement of CA 19-9 with the determination of other markers for sepsis and systemic inflammations, which have been regarded to date as typical tumour markers, is particularly suitable, especially with CA 125, S100B or S100A proteins involved in the regulation of inflammations, or with the determination of the novel sepsis markers inflammin (DE 101 19 804.3) and CHP (DE 101 31 922.3) described in the below-mentioned prior unpublished German Patent Applications of the Applicant, and/or with the determination of soluble cytokeratin fragments, in particular of the recently found soluble cytokeratin-1 fragments (sCY1F; DE 101 30 985.6) and of the known tumour markers CYFRA-21 or TPS, and/or with the determination of one or more of the above-mentioned prohormones. A simultaneous determination of the known inflammation parameter C-reactive protein (CRP) can also be provided. On the basis of the novel results described in this Application and the parallel Applications, a combination with measurements of known biomolecules or biomolecules still to be found, which are suitable as tissue- or organ-specific inflammation markers, should also be considered generally for fine sepsis diagnosis.

The content of said prior Applications of the Applicant is to be regarded as part of the disclosure of the present Application by express reference to these Applications.

CA 19-9 (cancer antigen 19-9) or GICA (gastrointestinal cancer antigen) is defined as a glycolipid which has a molar mass of about 36 kD and is identifiable by reaction with a certain specific monoclonal antibody (1116 NS 19-9; cf. Koprowski et al., Somatic Cell Genet 1979, 5:957-972). Its biological function is unknown.

Owing to its high specificity, it plays an important role in the diagnosis, therapeutic monitoring and monitoring of the course of gastrointestinal carcinomas, in particular in the case of pancreatic carcinoma, hepatobiliary carcinoma (carcinoma of the liver, carcinoma of the bile ducts) and carcinoma of the stomach (cf. Lothar Thomas (editor): Labor und Diagnose, Section 34.3, pages 966-969, 5th Edition, 1998, TH-Books Verlagsgesellschaft).

It is known that increased levels of CA 19-9 can also be measured in orders of magnitude of about 20% of cases also in some patients with nonmalignant inflammatory diseases, such as cholecystitis and obstructive icterus, cholelithiasis, cholecystolithiasis, acute chlolangitis, toxic hepatitis and other liver diseases (cf. Lothar Thomas, loc cit; M. J. Duffy, Ann Clin Biochem 1998; 35; 364-370).

According to our knowledge, no systematic CA 19-9 measurements have as yet been carried out in the case of patients suffering from sepsis, and nothing was known up to now concerning significantly increased measured values of the typical tumour markers CA 19-9 in the vast majority of cases in patients with systemic inflammations (sepsis).

A substantial increase in the CA 19-9 concentrations in the predominant number of sepsis patients was found for the first time in the determinations which are described in the following experimental report with reference to two figures.

Figure 2:
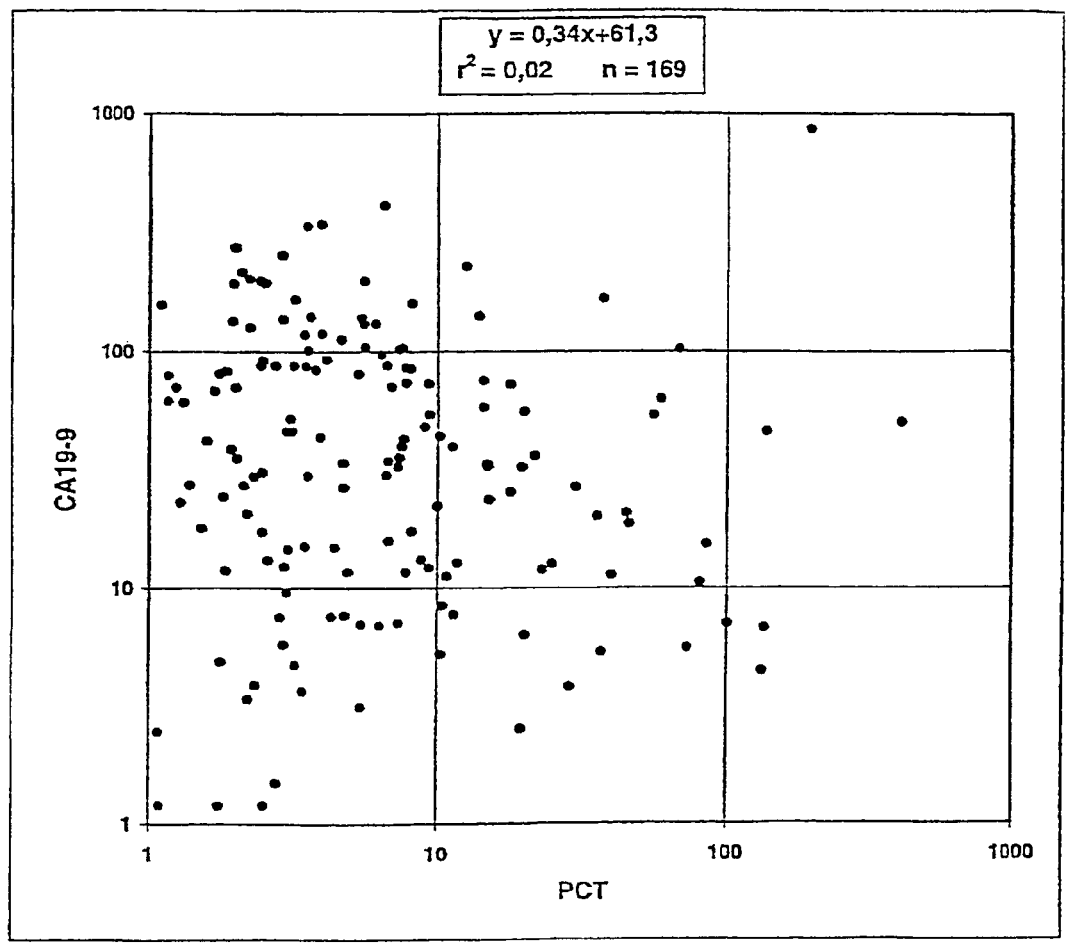

In the figures:

FIG. 1 shows the results of the determination of CA 19-9 in the sera of 171 sepsis patients in comparison with a group of 50 control persons (blood donors); and FIG. 2 shows the correlation of the results of the CA 19-9determinations of the 171 sepsis patients of FIG. 1 with the results of the procalcitonin determination.

Experimental Report:

The concentrations of the tumour marker CA 19-9 were measured in 171 sera of sepsis patients in whom high values of the sepsis marker procalcitonin (PCT) had been found, using a commercial assay for the determination of CA 19-9 (KRYPTOR-CA19-9 from B.R.A.H.M.S Diagnostica GmbH). In 62% of the sera, greatly increased CA 19-9 concentrations (more than 20 U/ml) were found.

A graph of the measured results is shown in FIG. 1.

If the CA 19-9 values measured for individual sera are compared with the values measured for PCT, no positive correlation is found in the sense that the highest CA 19-9 values are also found in sera in which high PCT concentrations were found. FIG. 2 shows the correlations found in the case of such a comparison. It is evident that high CA 19-9 values (upper third of the diagram) are obtained at moderate PCT concentrations, and moderate values for CA 19-9 at very high PCT concentrations (right third of the diagram).

The fact that the results of the CA 19-9 determination are substantially independent from those of the PCT determination shows that different effects are measured in spite of the increased values for both parameters in the case of sepsis, which means that the measurement of both parameters provides more information than the measurement of only one of the parameters.

The combination of the determination of CA 19-9 with that of one or more sepsis markers is therefore suitable for improving the fine diagnosis of sepsis and for improving the prognosis of the course of the disease and for therapy-accompanying monitoring of the course in sepsis patients, it clearly being hoped that the interpretation of the results of such combined determinations based on the exact evaluation of individual cases documented as completely as possible (with, for example, information about the type of infection, reason for and course of the sepsis disease, characteristic data on the age and sex of the patients) will be steadily improved with the number of cases evaluated.

The determination of CA 19-9 can be carried out by any desired suitable detection method, although the determination in a body fluid of a patient by an immunodiagnostic method using suitable selective antibodies appears to be the most advantageous from practical points of view. Commercial assays for the determination of CA 19-9 are already available and can also be used in the context of the present invention. Where necessary, good accuracy of measurement in the measuring range relevant for the sepsis diagnosis must be ensured.

Thus, the determination of CA 19-9 can be carried out for early differential diagnosis and for detection and for the preparation of a prognosis, for assessment of the degree of severity and for therapy-accompanying assessment of the course of sepsis, by determining the content of CA 19-9 in a sample of biological fluid of a patient in such a method and drawing conclusions about the presence of a sepsis from the detected presence and/or amount of CA 19-9 and correlating the result obtained with the severity, the progress of the sepsis and/or the tissue or organ most greatly affected by the sepsis and choosing the possible treatments accordingly and/or estimating the prospects of the treatments.

The invention claimed is:

1. A method for assisting in the diagnosis of sepsis, said method comprising testing a biological fluid of a patient who, based on clinical findings, has sepsis-associated symptoms, for an elevated amount of CA19-9 as compared to a control group, wherein an elevated amount of CA19-9 in said sample is indicative of sepsis.

2. The method of claim 1, wherein the elevated amount of CA19-9 is determined by an immunodiagnostic assay method.

3. The method of claim 1, wherein said method is carried out in the course of a multiparameter determination in which at the same time at least one further sepsis parameter is determined.

4. The method of claim 3, wherein said at least one further sepsis parameter determined in the course of the multiparameter determination is selected from the group consisting of procalcitonin, CA125, S100B, S100A proteins, CYFRA 21, TPS, soluble cytokeratin-1 fragments (sCY1F), inflammin, CHP, peptide prohormones and the C-reactive protein (CRP).

5. The method of claim 3, wherein said multiparameter determination is carried out as a simultaneous determination using a measuring apparatus operating according to the chip technology or immunochromatographic method.

6. The method according to claim 5, wherein said measuring apparatus provides a complex measured result and wherein the evaluation of said complex measured result is carried out using a computer program.

7. The method of claim 1, wherein said biological fluid is serum.

8. The method of claim 1, wherein said sepsis is a bacterial sepsis.

9. The method of claim 3, wherein said method is carried out in the course of a multiparameter determination in which at the same time other sepsis parameters are determined, and a result in the form of a set of measured variables is obtained and evaluated for sepsis diagnosis.

* * * * *

UNITED STATES PATENT AND TRADEMARK OFFICE
CERTIFICATE OF CORRECTION

PATENT NO. : 7,572,590 B2  Page 1 of 1
APPLICATION NO. : 10/496250
DATED : August 11, 2009
INVENTOR(S) : Andreas Bergmann It is certified that error appears in the above-identified patent and that said Letters Patent is hereby corrected as shown below:

On Title page Item Assignee (73): Delete "B.R.A.H.M.S. Aktiengesellschaft" and insert --B.R.A.H.M.S Aktiengesellschaft--

Signed and Sealed this

Twenty-second Day of December, 2009

David J. Kappos
*Director of the United States Patent and Trademark Office*